United States Patent [19]

Lohmueller et al.

[11] Patent Number: 4,732,918
[45] Date of Patent: Mar. 22, 1988

[54] HEAT INTERCHANGING PROCESS AND REACTOR THEREFOR

[75] Inventors: Reiner Lohmueller; Ulrich Lahne; Michael Heisel, all of Munich; Helmut Schneider, Gruenwald; Markus Raab, Germering; Karl Höbel, Geretsried, all of Fed. Rep. of Germany

[73] Assignee: Linde Aktiengesellschaft, Wiesbaden, Fed. Rep. of Germany

[21] Appl. No.: 724,702

[22] Filed: Apr. 18, 1985

[30] Foreign Application Priority Data

Apr. 18, 1984 [DE] Fed. Rep. of Germany ....... 3414717

[51] Int. Cl.$^4$ .............................................. C07C 1/04
[52] U.S. Cl. ..................................... 518/712; 422/201
[58] Field of Search .......................................... 518/712

[56] References Cited

U.S. PATENT DOCUMENTS

| 2,051,774 | 8/1936 | Kleinschmidt | 518/712 |
| 2,662,911 | 12/1953 | Dorschner et al. | 518/712 |
| 4,339,413 | 7/1982 | Lahne et al. | 518/712 |

FOREIGN PATENT DOCUMENTS 2848014  5/1980  Fed. Rep. of Germany.

OTHER PUBLICATIONS

Scholz, Linde Reports on Science and Technology 18 (1973) pp. 35–40.

*Primary Examiner*—Howard T. Mars
*Attorney, Agent, or Firm*—Millen & White

[57] ABSTRACT

For conducting exothermic catalytic reactions, e.g., production of methane from $CO_x$ and $H_2$, a reactor is cooled internally by indirect heat exchange with a single heat exchanger provided in the reactor feed inlet region with a gradually increasing surface intensity (defined as the product of the overall coefficient of thermal conductivity, (h), of the tube wall times the cooling surface density, $m^2/m^3$) reaching a maximum intensity at a central zone of the heat exchanger where the preponderant cooling occurs. A zone of gradually decreasing cooling surface intensity may also be provided at the outlet end of the reactor, and uncooled adiabatic zones may be incorporated in the zones immediate the inlet and outlet ends of the reactor.

19 Claims, 3 Drawing Figures

HEAT INTERCHANGING PROCESS AND REACTOR THEREFOR

BACKGROUND OF THE INVENTION

This invention relates to a process and apparatus for performing chemical reactions, e.g., methanation of carbon oxides with hydrogen, in a reactor containing a bed of catalyst, especially particulate solid catalyst, said reactor being further provided with indirect heat exchange means. The invention is particularly applicable to exothermic catalytic reactions, with the indirect heat exchange means being used for cooling the catalyst bed.

A reactor that can be used for performing such a process is described in DOS No. 2,848,014. In this reactor, two tube bundle heat exchangers are arranged in axially offset relationship within a catalyst bed; these heat exchangers can be charged with coolant independently of each other whereby different temperatures can be selected over the length of the catalyst bed. As an additional feature of this reactor, feed pipes for the reaction mixture are provided within the catalyst bed. This process involves a so-called cold-gas quench feed which constitutes additional cooling means for avoiding excessively high peak temperatures in the catalyst bed. The conventional reactor thus comprises three, more or less independently controllable cooling systems which, though ensuring a high degree of flexibility of temperature control, is very expensive to construct on the one hand and to equip with associated temperature control means on the other hand.

SUMMARY OF THE INVENTION

It is, therefore, an object of one aspect of the invention to provide an improved process of the type discussed above.

An object of another aspect of the invention is to provide a less costly reactor suitable for performing the process, which at the same time permits the reaction to be conducted safely.

Upon further study of the specification and appended claims, further objects and advantages of this invention will become apparent to those skilled in the art.

These objects are attained in the process aspect of the invention by providing that the catalyst bed is cooled by a single tubular heat exchanger having multiple cooling zones. Cooling is conducted in the inlet zone of the reactor, by heat exchange in a zone of increasing cooling surface intensity thereby reaching a maximum cooling surface intensity. The cooling is continued in a zone of constant maximum cooling surface intensity so that the preponderance of cooling of the catalyst bed is conducted at this maximum intensity. By "cooling surface intensity" in the context of this invention is meant the product of the overall coefficient of thermal conductivity of the tube wall (h) times the cooling surface density ($A_D$), i.e., the cooling surface per unit volume of the bed. In the preferred embodiment h is constant, thereby making the cooling surface density the controllable variable.

An essential feature of the process of this invention is that cooling is accomplished by means of a single heat exchanger which does not exhibit a uniform cooling surface intensity but rather is designed so that reduced cooling takes place in the entrance zone of the reactor. The effect of the reduced cooling zone is that the reaction temperature within the catalyst bed will rise in the entrance zone of the reactor more rapidly than in the downstream zone of maximum cooling surface intensity. In specific cases, it is necessary, of course, not to exceed maximum design temperatures, the latter depending on the type of reaction to be conducted, the catalyst properties, etc. An advantage of the rapid rise in temperature in the entrance zone of the reactor is that the reaction velocity is thereby increased and accordingly, in the final analysis, less catalyst volume is required.

The region of gradually increasing cooling surface intensity or density in the entrance zone of the reactor comprises preferably between 5 and 50%, especially between 10 and 20% of the length of the cooled catalyst bed. Of course, the particular value in any given case will depend on the type of reaction to be performed and on the special process conditions prevailing therein.

According to a preferred advantageous feature of the invention, a zone of gradually decreasing cooling surface intensity is also provided in the outlet zone of the catalyst bed. The reduced cooling surface intensity in the outlet zone of the reactor results in, as compared with a uniform cooling surface intensity up to the outlet end, a rise in the temperature of the reaction mixture and thus, again, in an increase in the reaction velocity. This manner of operating the process is advantageous, in particular, if the reaction velocity within the cooled catalyst zone decreases severely toward the outlet end of the reactor. The unreacted proportion of the reactants can, in this case, react more favorably with increasing temperatures until the reaction equilibrium has been attained, as compared to the case of maximum cooling being applied throughout the remainder of the bed. In other words, with uniform cooling, a longer residence time of the reactants and thus a larger reactor volume would otherwise be necessary.

The zone of gradually decreasing cooling surface intensity or density ranges between 5 and 30%, preferably between 10 and 20% of the length of the catalyst bed.

The increased outlet temperature from the reactor by virtue of reduced cooling in the outlet zone generally also provides another process advantage. Conventionally, as high a proportion as possible of the heat content of the hot reaction product is recovered by indirect heat exchange. Therefore, with a rise in the outlet temperature, a smaller heat exchanger can be provided for this heat exchange.

In another preferred feature of the process aspect of the invention, the above-described effect of the temperature control in the inlet as well as outlet zones of the reactor is supplemented by providing that the less cooled zones of the catalyst bed are in communication with uncooled, adiabatically operated regions of the catalyst bed: upstream of the inlet cooling and downstream of the outlet cooling.

The process of this invention is especially suitable for methanizing a synthesis gas containing hydrogen and carbon oxides, for carbon monoxide conversion, and for other reactions having a comparable exothermicity.

It can be seen from the above discussion of the invention that the essential feature of the invention resides in subjecting the entrance and preferably the outlet zone as well, of the catalyst bed to reduced cooling. Since the use of a graduated cooling, i.e., gradually decreasing and/or increasing cooling zones, along with maximum cooling zones within a single heat exchanger is the critical feature of the invention, versions of the process and apparatus aspects of the invention are contemplated wherein, with the cooling surface density remaining constant, reduced heat transfer is effected by modifying the conductivity h of the heat exchange tubes, e.g., by incorporating insulation thereon or using different materials for the tubes in different cooling zones.

According to the apparatus aspect of the invention, a reactor especially constructed for conducting the process of this invention comprises an essentially vertically disposed reactor housing containing a catalyst bed to be traversed substantially in the axial direction by a flow of a reaction mixture, with a single tube and sheet heat-exchanger being embedded in this catalyst bed. The heat exchanger is an axially oriented, wound tube bundle heat exchanger having at least in its central zone an essentially constant cooling surface density by virtue of a uniform arrangement of the winding of the heat-exchange tubes. At the end of this heat exchanger proximate the feed inlet there is provided a zone of decreasing cooling surface density. This zone of decreasing $A_D$ is designed, for example, by arranging the heat transfer tubes so that they are wound with an increasing pitch, i.e., less tightly wound, and/or by decreasing the angle of the tubes with respect to the axis of the reactor.

It is advantageous in many cases to design the reactor so that the end of the heat exchanger facing the outlet zone of the reactor also exhibits a decreasing $A_D$, for which purpose the heat-exchange tubes are conducted through this region of the catalyst bed with an increasing winding pitch and/or increasing axial alignment.

The zone of constant cooling surface density constituting the central region of the heat exchanger extends normally over 40–95%, preferably between 60 and 85% of the length of the heat exchanger, whereas the zone of variable cooling surface density constitutes the remainder.

In general, the change of cooling surface density or intensity in the variable zone is preferably about 30 to 80 especially about 50 to 70 m$^2$/m$^3$ per vertical meter within the variable cooling zone. The cooling surface density or intensity of the tubes rises gradually, slowly or rapidly from 0 to 100% of the maximum cooling surface density or intensity.

In an advantageous structural embodiment of the reactor of this invention, the heat exchanger is wound onto a core tube which is employed to convey the coolant to the heat-exchange tubes. One end of the core tube in this construction is provided with a flow reversal chamber sealed with respect to the catalyst bed, said chamber comprising a first tube sheet into which the ends of heat-exchange tubes are affixed. This structural arrangement makes it possible to effect feeding as well as discharging of coolant from a single end of the reactor. The coolant, conducted from the flow reversal chamber via the first tube sheet into the heat-exchange tubes is withdrawn at the outlet end of the heat exchanger via a second tube sheet attached to the core tube. The coolant is then withdrawn from the reactor by way of a central discharge conduit. The tube sheets can be designed in the conventional planar configuration, or they can also be curved which may be more advantageous in some cases for introducing the cooling tubes into the tube sheets and/or because of pressure considerations.

A preferred feature of the reactor of this invention provides that the tube sheets have a smaller diameter than the outside diameter of the tube bundle heat exchanger. It is especially advantageous in this connection to provide that the diameters of the tube sheets correspond approximately to the inner diameter of the wound heat exchanger, thereby facilitating the incorporation of the tube sheets within the catalyst bed on the one hand and providing a smaller obstruction to the flow of the reaction mixture and the reaction product. Thus, it is especially preferred for the diameter of the tube sheets to be about 25 to 75%, especially 30 to 50% of the outside diameter of the tube bundle heat exchanger. It is also advantageous for the heat-exchange tubes to be essentially parallel to the axis of the reactor where the tubes terminate in the tube sheets. This means that the tubes, wound in spiral shape in the central region of the heat exchanger, have a different alignment in the zone of reduced cooling surface density and pass over, from a uniform, helical configuration, into one having a greater pitch and optionally a reduced radius, and also terminate, finally, with an essentially axial alignment*. In general, in the central region of the heat exchanger, the angle of the helicaly wound tubes with respect to the axis of the reactor is about 5 to 45, preferably 10° to 20° Wound heat exchangers of uniform pitch are generally conventional, and for further details, attention is invited to "Linde Reports on Science and Technology", no. 18, 1973, p. 35 to 40.

*or in case of a spherical tube sheet an essential radial alignment in respect to the tube sheet.

BRIEF DESCRIPTION OF THE DRAWINGS

Various other objects, features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION OF DRAWINGS

Figure 1:
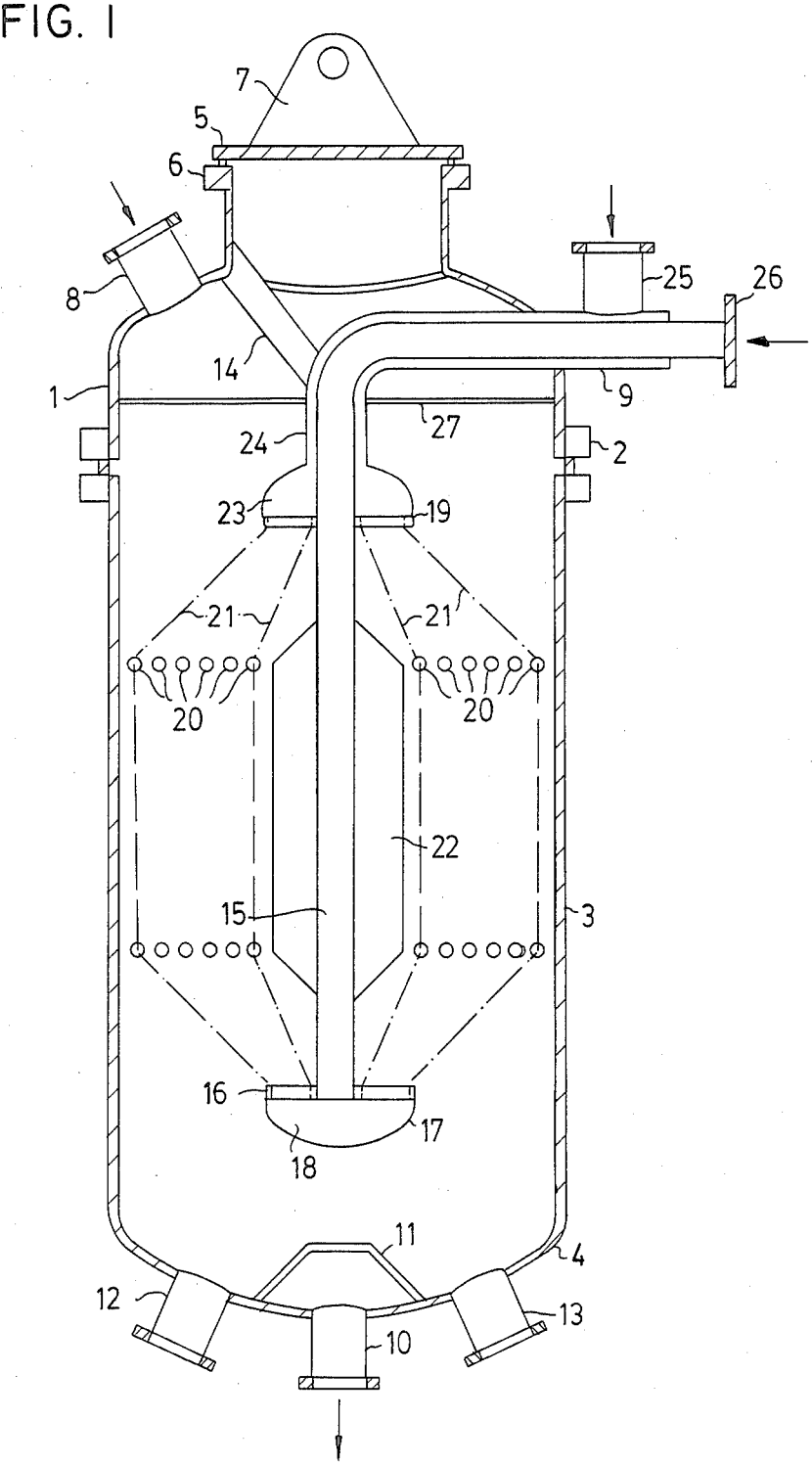
FIG. 1 is a partial cross section, schematic elevational view of a preferred reactor according to this invention.

The housing of the reactor illustrated in FIG. 1 comprises an upper dome, (e.g., a dished head), a vertically arranged, cylindrical shell 3 connected to the upper dome by a flange connection and having at the bottom a welded-on, bottom dome 4. The upper dome 1 comprises as the top closure, a horizontally arranged detachable lid 5 joined by a flange 6. Gripping means 7 are mounted to the lid 5 so that, for example, a crane can be used for moving the lid 5, or the lid 5 plus the flanged-on dome 1 and the internal structure of the reactor attached thereto, or even the entire reactor. The upper dome further comprises a feed inlet connection, or optionally several feed inlet pipe connections 8 uniformly distributed along the circumference of the hood for introducing reaction mixture into the reactor. An opening is also provided in the upper dome to receive the coolant conduit 9.

The lower dome 4 connected to the cylindrical shell 3 comprises an outlet connection 10 for discharging reaction product and a screen-like, gas-permeable structure 11 to prevent catalyst from being discharged with the product. In addition several pipe outlets 12, 13 uniformly distributed over the circumference of the bottom dome are sealed by blind flanges except when they are used to empty the catalyst bed from the reactor. To ensure complete emptying, the catalyst impermeable screen structure 11 is designed within the reactor in the form of a truncated cone, the base of which lies in the proximity of the pipe outlets 12, 13.

The reactor housing can optionally be provided entirely or partially with thermal insulation, e.g., a conventional blanket, not illustrated in the figure, or it can also be designed with a jacket resulting in a catalyst-free annular chamber between the two reactor jackets.

The reactor contains a wound tube bundle heat exchanger, suspended at the dome 1 by a mounting element 14 and by the cooling pipe 9 welded to the dome 1. The tubes are wound onto a centrally arranged core tube through which extends a cooling pipe 15. At the lower end, a tube sheet 16 attached to the cooling pipe 15 and a curved bonnet welded to the tube sheet, form a flow reversal chamber 18 for coolant conducted downwardly through cooling pipe 15 entering the tube sheet 16 and then upwardly into the cooling tubes. The bonnet 17 can optionally be provided with thermal insulation if cooling of the surrounding catalyst bed at this point is undesirable. Another tube sheet 19 is centrally attached to the cooling pipe 15 in the upper zone of the shell 3. The tube bundles 20 are thus fixed between tube sheet 16 and tube sheet 19, the position of these tube bundles being indicated within the reactor by the dot-dash lines 21. In FIG. 1, the tube cross sections are illustrated only at the beginning and at the end of the uniformly wound tubes. In this zone, the cooling tubes are wound onto a further core tube 22 attached to the cooling pipe 15. The core tube 22 is connected in a gastight fashion to the cooling pipe 15 to avoid undesirable short circuiting of the reaction mixture.

The cooling tubes have a diameter of between 8 and 25 mm, especially of between 10 and 15 mm, when cooling a methanization reaction with water boiling under pressure, and they are spaced from one another in the axial and radial directions respectively by about twice the tube diameter. The dimensioning depends, in a particular case, on the specific feed gas, the particle size and activity of the catalyst, and other process parameters.

The region of the heat exchanger wound onto the core tube 22, exhibiting a uniform cooling surface density, is followed by transition zones with variable cooling surface densities at the top and at the bottom. In this arrangement, the diameter of the heat exchanger decreases substantially from the diameter of the reactor to the diameter of the tube sheets 16 and 19, respectively. The tubes 20, arranged in the region of the core tube 22 in a helical configuration, are deflected for this purpose and finally terminate in the axial direction into the tube sheets.

The upper tube sheet 19 is connected to a coolant discharge conduit 24, arranged concentrically around the core tube 15, by way of a bonnet 23 which is optionally thermally insulated, just as the lower bonnet hood 17. The concentrically extending conduits 15 and 24 are bent in the zone of the upper dome so as to extend laterally out of the latter. The pipe 24 merges into the above-mentioned pipe 9. The pipe 9 can be connected, via an outlet pipe connection 25, to a further coolant discharge conduit, while the inlet pipe connection 26 connected to conduit 15 can be placed in communication with a coolant feed conduit. If desired, the heated heat exchange fluid can be cooled and returned to the reactor by any conventional cooling cycle or the like.

The reactor is filled up to line 27 with the particulate catalyst. Above the bed, a suitable arrangement for flow distribution can be provided for uniform charging with reaction mixture (this not being illustrated in the figure for reasons of simplicity). For filling the reactor with catalyst, the lid 5 can be removed.

During operation of the reactor shown in FIG. 1, the reaction mixture first flows through an uncooled catalyst zone, the length of which can optionally be varied by the filling level (line 27). An adiabatic reaction occurs in the uncooled reaction zone, and a relatively high temperature is quickly attained. After passing through this zone, the reaction mixture is first subjected to a relatively minor cooling, whereafter a uniform, intensive cooling occurs after entering into the portion of the heat exchanger wound onto the core tube 22. After leaving this region, the reaction mixture first flows again through a zone of reduced cooling and finally, below the tube sheet 16, passes through an uncooled region so that again an adiabatic reaction occurs. The reaction mixture, after passing through the screen device 11, is then withdrawn from the reactor via outlet 10.

Figure 2:
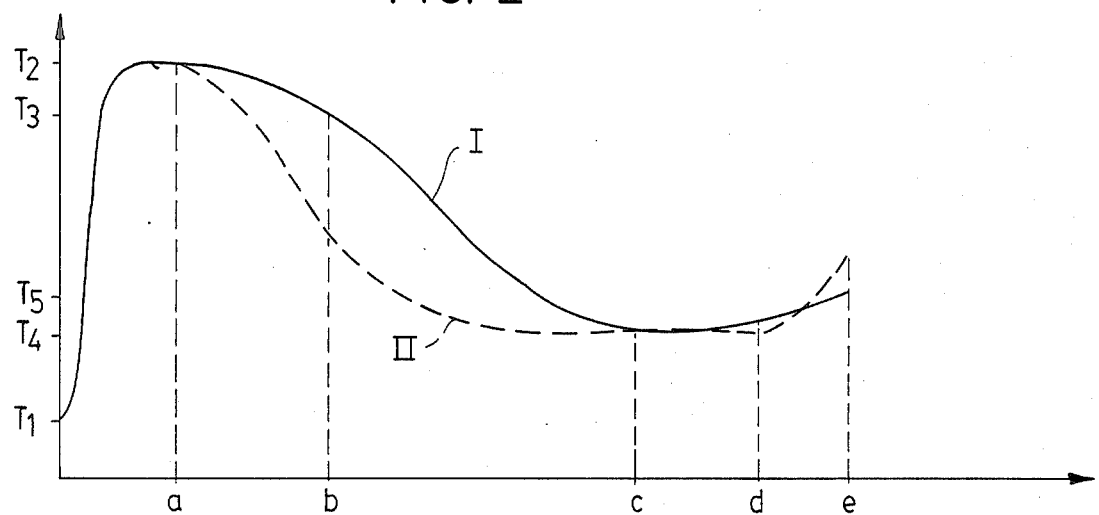
FIG. 2 is a graph of the temperature in the reactor of FIG. 1 during a methanization reaction, as a function of the distance from the feed inlet.

The temperature curve obtained during a methanizing reaction is illustrated qualitatively in FIG. 2. The reaction mixture enters the catalyst bed at 27 with an entrance temperature $T_1$ and, owing to the lack of cooling, is heated adiabatically up to the high temperature $T_2$ after a very short reaction path. After passing through the uncooled zone (a in FIG. 2), the temperature of the reaction mixture will drop to temperature $T_3$ in the subsequent catalyst zone operated with reduced cooling (b in FIG. 2) in correspondence with curve I in FIG. 2. Subsequently the reaction mixture enters the region wound onto the core tube 22, operated at maximum cooling, (region b-c in FIG. 2) and here the temperature drops to the value $T_4$ before it is again slightly heated up in the subsequent zone of reduced cooling (region c-d in FIG. 2). The reaction mixture is finally heated up to the outlet temperature $T_5$ in the uncooled outlet zone of the catalyst bed (region d-e in FIG. 2).

For purposes of comparison, dashed line II in FIG. 2 illustrates the temperature curve assuming that the entire region between the tube plates 19 and 16 is operated at maximum cooling. The temperature in this case drops relatively quickly to the value $T_4$, corresponding to a substantially isothermal reaction, and the conversion is conducted at a correspondingly lower reaction ratio. With the length of the cooling zone being the same, this can mean that too little reaction mixture is converted, or that, with the use of a highly active catalyst, the conversion goal cannot be attained in the adiabatically operated final section and/or that this catalyst section will be damaged irreversibly.

Thus, by conducting the reaction in accordance with the temperature profile of curve I, the high temperature achieved in the entrance zone of the reactor which decreases only gradually results in a very high reaction velocity. However, since a high conversion rate in case of reactions determined by equilibrium, such as methanization, for example, can be accomplished only if the outlet temperature is relatively low, it is necessary in order to achieve this objective, to aim for a relatively low outlet temperature. The adiabatic final reaction (region d-e) seems initially to run counter to this requirement, but it leads to a high product yield, with an incomplete reaction in the region b-c, since the unreacted proportion, with an increasing temperature, up to equilibrium, can be reacted more favorably than under isothermal conditions, i.e., under isothermal conditions at a lower temperature, a longer residence time and thus a larger reactor volume would be required.

Figure 3:
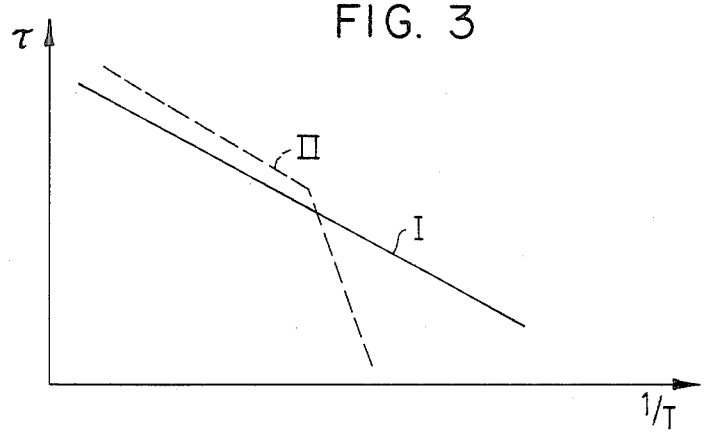
FIG. 3 is a graph of the rate of reaction (reaction velocity) as a function of the reciprocal of temperature in a methanization reaction.

A peculiarity observed in methanization is illustrated in qualitative form with reference to FIG. 3. The reaction velocity $r$ is plotted as a function of the reciprocal value of the absolute temperature. The normal Arrhenius curve constitutes a reduction in reaction velocity with the temperature, in accordance with line I. However, it has been discovered, when conducting methanization with the use of various commercially available methanization catalysts, that the reaction velocity drops severely as the temperature decreases to on the order of about 250° to 350° C., depending on the particular catalyst-support combination. This means that with a conventional, uniform cooling operation within a catalyst zone, only a low methane yield can be obtained. Therefore, it has been conventionally necessary, to operate in a multistage fashion, in other words to connect a second reactor after the first, in order to obtain a high methane yield. The use of the reactor according to this invention, in contrast thereto, makes it possible to obtain very high yields of methane even in a single-stage operation.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius.

EXAMPLE

The following description involves a specific example wherein a feed gas is provided consisting essentially of 37.5% hydrogen (percentages refer in each case to percent by volume), 12.5% carbon monoxide, 12.4% carbon dioxide, 12.5% methane, 0.1% nitrogen, and 25.0% steam, and which is under a pressure of 10 bar and at a temperature of 310° C. This feed gas is conducted at a rate per unit volume ranging between 6,000 and 10,000 Nm$^3$/m$^3$ of catalyst per hour through the first adiabatic reaction zone, then at between 4,000 and 8,000 Nm$^3$/m$^3$ of catalyst per hour through the cooled zones, and then through a second adiabatically operated zone. The reactor employed corresponds to the embodiment illustrated in FIG. 1.

In the first adiabatic catalyst zone on the entrance side constituting about 5 to 10% of the length of the catalyst bed, the temperature is increased from 310° C. up to a high of about 615° C. The reaction mixture is then passed through the zone of increasing cooling surface area density constituting about 10 to 15% of the length of the catalyst bed, to reach a maximum surface area density where the reaction mixture attains a temperature of about 550°C. This latter temperature is then lowered to about 320° C. as the gas is withdrawn from the zone of uniform cooling, the latter zone characterized by the cooling tubes being wound onto the core tube 22 at the maximum cooling surface density. Here, the gaseous mixture flowing through the reactor consists essentially of 16.3% hydrogen, 0.7% carbon monoxide, 18.8% carbon dioxide, 26.2% methane, 0.1% nitrogen, and 37.9% steam. From the downstream end of the uniform cooling zone to the outlet end of the reactor, the temperature increases in a zone of decreasing cooling amounting to about 10% of the length of the catalyst bed to reach a temperature of 350° C. From the latter zone the reaction mixture is passed through an adiabatic zone constituting about 10 to 20% (including the lower dome) of the length of the catalyst bed, so that the reaction product finally leaves the reactor at a temperature of 410° C. and under a pressure of 8.5 bar. This product contains 8.9% hydrogen, 0.4% carbon monoxide, 17.8% carbon dioxide, 29.4% methane, 0.1% nitrogen, and 43.4% steam. After the conventional steps of cooling and separation of carbon dioxide and steam, a product is finally obtained containing 22.7% hydrogen, 1% carbon monoxide, 1% carbon dioxide, 75% methane, and 0.3% nitrogen.

If, for purposes of comparison, the exit gas from the zone of uniform cooling were to be utilized directly as the product gas, then a product gas would be obtained, after cooling, separation of carbon dioxide and water, which contains 37.3% hydrogen, 1.6% carbon monoxide, 0.9% carbon dioxide, 0.2% nitrogen, and only 60% methane.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions. For example, this invention can also be used for endothermic reactions where a heating fluid instead of a cooling fluid is passed through the heat exchanger.

What is claimed is:

1. In a process comprising conducting methanization of a synthesis gas consisiting essentially of carbon oxides and hydrogen in a reactor containing a feed inlet zone at one end, a product outlet zone at the other end and a catalyst bed cooled by indirect heat exchange wherein a coolant is conducted crosscurrently through the catalyst bed, the improvement which comprises cooling the bed in a zone of gradually increasing cooling surface intensity near the feed inlet zone of the reactor, said zone of gradually increasing cooling surface intensity ranges between 5 and 20% of the length of the cooled catalyst bed, said cooling surface intensity reaching a maximum value, and conducting the preponderant cooling of the catalyst bed at said maximum value of cooling surface intensity in the central part of the reactor, all of said cooling being conducted in a single heat exchanger.

2. A process according to claim 1, wherein the zone of gradually increasing cooling surface intensity if provided by a zone of gradually increasing cooling surface density.

3. A process according to claim 1, wherein the zone of gradually increasing cooling surface intensity ranges between 10 and 20% of the length of the cooled catalyst bed.

4. A process according to claim 2, wherein the zone of gradually increasing cooling surface density ranges between 5 and 20% of the length of the cooled catalyst bed.

5. A process according to claim 2, wherein the zone of gradually increasing cooling surface density ranges between 10 and 20% of the length of the cooled catalyst bed.

6. A process according to claim 1, wherein the catalyst bed is cooled downstream of the preponderant cooling zone in a zone of gradually decreasing cooling surface intensity near the product outlet zone of the reactor.

7. A process according to claim 6, wherein the cooling surface intensity is the cooling surface density.

8. A process according to claim 6, wherein the zone of decreasing cooling surface intensity ranges between 5 and 30% of the length of the cooled catalyst filling.

9. A process according to claim 7, wherein the zone of decreasing cooling surface density ranges between 5 and 30% of the length of the cooled catalyst filling.

10. A process according to claim 8, wherein the zone of decreasing cooling surface intensity ranges between 10 and 20% of the length of the cooled catalyst filling.

11. A process according to claim 7, wherein the zone of decreasing cooling surface density ranges between 10 and 20% of the length of the cooled catalyst filling.

12. A process according to claim 1, wherein the zone of gradually increasing cooling surface intensity near the feed inlet zone of the reactor is preceded by an uncooled, adiabatically operated catalyst zone.

13. A process according to claim 6, wherein the zone of gradually decreasing cooling surface intensity near the product outlet zone of the reactor is followed by an uncooled, adiabatically operated catalyst zone.

14. A process according to claim 6, wherein the zone gradually increasing cooling surface intensity near the feed inlet zone of the reactor is preceded by an uncooled, adiabatically operated catalyst zone.

15. A process according to claim 14, wherein the zone of gradually decreasing cooling surface intensity near the product outlet zone of the reactor is followed by an uncooled, adiabatically operated catalyst zone.

16. A process according to claim 1, wherein the cooling surface intensity in said zone of gradually increasing cooling surface intensity changes at a rate of 30 to 80 $m^2/m^3$ per vertical meter.

17. A process according to claim 16, wherein said rate is 50 to 70 $m^2/m^3$ per vertical meter.

18. A process according to claim 2, wherein the cooling surface density in said zone of gradually increasing cooling surface density changes at a rate of 30 to 80 $m^2/m^3$ per vertical meter.

19. A process according to claim 18, wherein said rate is 50 to 70 $m^2/m^3$ per vertical meter.

* * * * *